United States Patent [19]

Heiliger

[11] Patent Number: 5,242,413
[45] Date of Patent: Sep. 7, 1993

[54] DISC VALVE FOR A CATHETER

[75] Inventor: Raymund Heiliger, Herzogenrath, Fed. Rep. of Germany

[73] Assignee: Vygon GmbH & Co. KG, Aachen, Fed. Rep. of Germany

[21] Appl. No.: 917,987

[22] Filed: Jul. 24, 1992

[51] Int. Cl.⁵ .............................. A61M 5/178
[52] U.S. Cl. ................................. 604/167; 604/256
[58] Field of Search .................... 604/167, 256; 251/149.1; 137/849

[56] References Cited

U.S. PATENT DOCUMENTS

| 4,655,752 | 4/1987 | Honkanen et al. | 604/167 |
| 4,705,511 | 11/1987 | Kocak | 604/167 |
| 5,114,408 | 5/1992 | Fleischhaker et al. | 604/256 |

FOREIGN PATENT DOCUMENTS 9110459  7/1991  World Int. Prop. O. .......... 604/256

Primary Examiner—John D. Yasko
Assistant Examiner—Anthony Gutowski
Attorney, Agent, or Firm—Mark T. Basseches

[57] ABSTRACT

A valve element adapted to be positioned in the infeed for a catheter is disclosed. By slits in Y arrangement relative to each other, an automatically closable passage opening is formed therein. The passage is especially easy to locate for the catheter tip due to the fact that the valve element is provided on its proximal side with a truncated cone-shaped recess. In addition, due to the recess the flexibility of the gussets of material defined by the slits is enhanced, which gussets sealingly hug the outside of the catheter when the catheter is present The distal face of the valve may be provided also with a truncated cone-shaped recess.

3 Claims, 1 Drawing Sheet

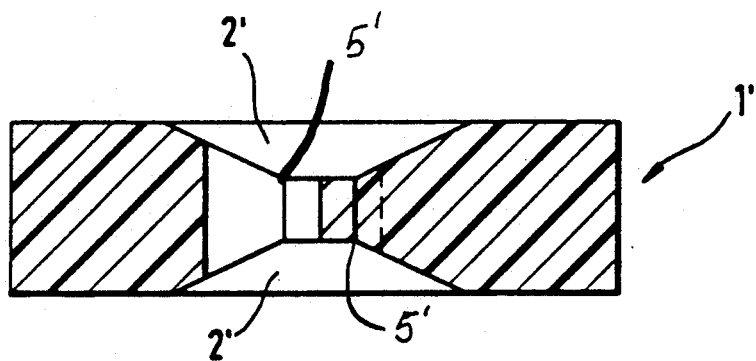
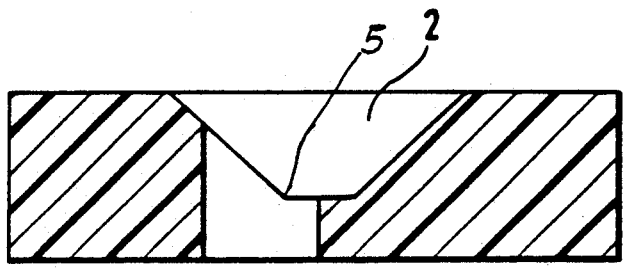
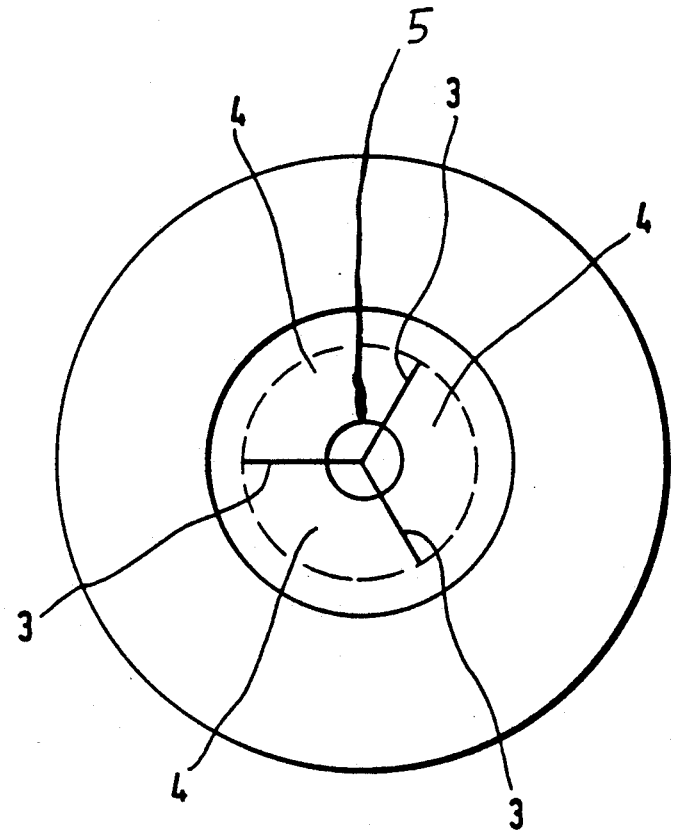

DISC VALVE FOR A CATHETER

BACKGROUND OF THE INVENTION

This invention relates to an infeed for a catheter of the type which includes a valve element which has an automatically closable passage for sealingly receiving the catheter. The passage opening is formed by slits which are oriented radially outward from the center axis of the circular disk-shaped valve element and which extend substantially axially through the valve element.

PRIOR ART

A catheter infeed is known from U.S. Pat. No. 3,585,996 and consists of a large number of separate parts, this being a disadvantage with respect to manufacture, handling and maintenance. In this known infeed the seal is effected not directly at the catheter but at a special connecting piece, where a second seal provided with a Y-shaped slit is located. The seals cooperate only when a catheter is present to provide a reliable seal against the blood pressure.

From DE 25 23 511C2 an infeed of the above described kind is known having a reduced number of separate parts making possible a fast and reliable seal on the one hand directly at an introduced catheter and on the other hand, in the absence of a catheter, against the blood pressure. This known infeed is also equipped with two seals arranged side by side. The first seal, made of elastic material, is provided with an opening for the introduction of the catheter and has a somewhat smaller diameter than the catheter, so that, with the catheter introduced, the seal applies against it sealingly. The second seal, also made of elastic material, has a Y-shaped slit which, in the absence of a catheter, is to brace against the first adjacently positioned seal. With this infeed, despite the second seal, a leak can be avoided only if the central opening in the first seal is adapted to the catheter with sufficient precision. If, however, catheters of different diameters are to be used, an effective seal cannot be dependably achieved.

Lastly there is known from DE 34 01 440 C2 an infeed of the initially described kind which is to ensure a liquidproof seal also for catheters with greatly different outside diameters. To this end, the one-piece valve element made of elastic material is provided with a first slit opening only toward a first end face and with a second slit opening only toward a second end face of the valve. The two slits thus each extend in axial direction only over a partial region of the valve element. They cross inside the valve element and intersect at points offset from the end faces of the valve element or respectively lying between them. A major disadvantage of this infeed is to be seen in that the design of the valve element makes the introduction of a catheter quite difficult. If the tip of the catheter to be introduced misses the crossing-point of the slits in the valve element, or if due to a slight inclination the center axis of the catheter forms with the center axis of the infeed only a small angle, the catheter tip, although impinging on the elastic material of the valve element, but it cannot be introduced properly. The valve element may even be damaged and become inoperable through repeated unsuccessful attempts at introducing the catheter.

SUMMARY OF THE INVENTION

It is an object of the invention to design a valve for the infeed of a catheter in such a way that a liquidproof closure can be ensured even when using catheters of greatly differing outside diameters, as well as in the absence of a catheter.

A further object of the invention is the provision of a catheter valve wherein correct introduction of the catheter is greatly facilitated and is possible even if the catheter tip is not coaxially guided through the infeed.

For the solution of this problem there is provided a valve for catheter infeed comprising a circular disc-shaped elastic element having Y-shaped slits, normally sealed and intersecting at a central location of the disc. At least the proximal face of the disc is formed with a recess in the shape of a truncated cone, the base of the cone being coincident with the proximal face, the dedendum circle of the cone being located intermediate the proximal and distal surfaces of the disc. The cone axis is aligned with the intersection of the slits and is perpendicular to the disc surfaces. The radial extent of the slits is preferably less than the radius of the base circle of the cone, but greater than the dedendum circle. Optionally, the distal face of the disc is formed by a second cone shaped recess as described, in which case the dedendum circles of the recesses are each located at a depth of about one-third the thickness of the disc.

Due to the funnel type recess in the valve element, it is sufficient for proper introduction of the catheter if, to begin with, the catheter tip impinges on the valve element within the base circle of the recess and is then guided by the oblique lateral wall of the recess onto the bottom of the recess defined by the dedendum circle. There, the slotted elastic valve element material offers little resistance to the catheter tip, so that a low axial feed force exerted on the catheter suffices to push the catheter forward through the infeed.

As a result of this structure, in the slotted valve element region there result gussets of material of greatly reduced wall thickness as compared with the valve element thickness, in the form of circle segments having correspondingly increased flexibility. The gussets therefore hug the outer circumference of the catheter and greatly support the sealing action.

According to a variant of the invention, the radial extent of the slits is smaller than the radius of the base circle and larger than the radius of the dedendum circle of the recess.

Due to this design, the gussets are connected with the rest of the valve element over a correspondingly larger connecting cross-section. This brings about an increase of the restoring force of the gussets returning them to their starting position as soon as the catheter is removed from the infeed.

The flexibility of the gussets can be enhanced further by the fact that according to an additional development of the invention there originates from each of the two end faces of the valve element a truncated cone-shaped recess.

With this variant, too, the enlarged connecting cross-section of the gussets at the rest of the valve element can be preserved, especially as the size thereof can be influenced essentially by the radial extent of the slits.

Lastly, a development of the invention further provides that the sum of the parallel distances between the base circle and the dedendum circle of both truncated cone-shaped recesses is smaller that the height of the valve element.

By this design it is ensured that as a result of the recesses in the region of the projection of the dedendum circles the gussets are not entirely eliminated, but that in the absence of a catheter the infeed remains just as tightly closed by the gussets as in the presence of the catheter.

BRIEF DESCRIPTION OF DRAWINGS

In the drawings, two examples of realization of a valve element of an infeed according to the invention are illustrated on an enlarged scale.

FIG. 1 shows a valve element with a recess in transverse section;

FIG. 2, a valve element with two recesses in transverse section;

FIG. 3 is a top view onto the valve element per FIG. 1 of respectively FIG. 2.

DETAILED DESCRIPTION OF DRAWINGS

In the housing (not shown) of an infeed a circular disc-shaped valve element 1 or respectively 1' of elastic material is inserted.

On its proximal side the valve element 1 is provided with a truncated cone-shaped recess 2, the dedendum circle 5 of which lies approximately at mid-height of the valve element 1.

The valve element 1' is provided on each of its two end faces with a truncated cone-shaped recess 2', the respective dedendum circles 5' of which lie at about one-third the height of the valve element 1'.

Slits 3 extending radially from the center axis of the valve element 1 or respectively 1' and arranged in Y-form relative to each other generate segment type gussets of material 4 which, as a result of the elasticity of the valve element 1, can indeed be displaced by a catheter introduced into the infeed, but which brace themselves sealingly against the outside of the catheter and, as soon as the catheter is removed from the infeed, resume the starting position shown in the drawing and likewise seal the infeed. Preferably, the radius of the slits 3 is greater than the radius of dedendum circles (5,5'), but less than the radius of the base portion of recesses 2,2'.

From the foregoing description it will be apparent that there is provided, in accordance with the invention, a simple readily manufactured valve element for a catheter infeed which provides effective sealing action both when a catheter is inserted and after it is withdrawn. The valve facilitates introduction of catheters of a variety of sizes by the oblique walls of the recesses, and by the fact that the gussets are readily deflected due to reduced thickness.

As will be apparent to a skilled worker familiarized with the instant disclosure, numerous variations in details of construction may be made without departing from the spirit of the invention. Thus, the invention is to be broadly construed within the scope of the appended claims.

Having thus described the invention and illustrated its use, what is claimed as new and desired to be secured by Letter Patent is:

1. In a normally closed self-sealing circular disc-shaped elastic valve element for penetrably and sealingly receiving the tip of a catheter, said element having distal and proximal end surfaces and including an automatically closing passage extending between said end surfaces and adapted to sealingly embrace a catheter inserted therethrough, said valve element including a plurality of radially oriented angularly offset slits extending axially through the depth of said element and meeting at a point located centrally of aid element, the improvement which comprises a first truncated cone-shaped recess formed in one of said end surfaces, the axis of said recess being perpendicular to aid end surface and aligned with said point, said recess having a base circle coinciding with said one surface, and a dedendum circle disposed part way through the thickness of said element, a second truncated cone-shaped recess formed in the other said end surface, said second recess being coaxially aligned with said first recess and having a base circle coincident with said other end surface and a dedendum circle disposed in spaced parallel relation to the dedendum circle of said first recess, the radial extent of said slits being smaller than the radius of said base circle and larger than the radius of said dedendum circle.

2. A valve element in accordance with claim 1 wherein said slits are three in number and together define a Y-shaped configuration.

3. A valve element in accordance with claim 1 wherein the dedendum circles of said recesses are disposed, at a depth of generally one-third the thickness of said valve element.

* * * * *